(12) United States Patent
Naiberk et al.

(10) Patent No.: US 9,918,923 B1
(45) Date of Patent: Mar. 20, 2018

(54) LEAVE-ON HAIR STYLING COMPOSITIONS AND METHODS OF USE

(71) Applicant: L'OREAL, Paris (FR)

(72) Inventors: Emma Naiberk, Clark, NJ (US); Vanessa Decarlo, Clark, NJ (US); Anna Botto, Clark, NJ (US); Azizah Suleiman, Clark, NJ (US); Anand Mahadeshwar, Scotch Plains, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/445,342

(22) Filed: Feb. 28, 2017

(51) Int. Cl.
| | |
|---|---|
| *A61K 8/73* | (2006.01) |
| *A61Q 5/06* | (2006.01) |
| *A61K 8/37* | (2006.01) |
| *A61K 8/34* | (2006.01) |

(52) U.S. Cl.
CPC .............. *A61K 8/737* (2013.01); *A61K 8/345* (2013.01); *A61K 8/37* (2013.01); *A61K 8/73* (2013.01); *A61K 8/731* (2013.01); *A61Q 5/06* (2013.01); *A61K 2800/30* (2013.01); *A61K 2800/34* (2013.01)

(58) Field of Classification Search
None
See application file for complete search history.

(56) References Cited

U.S. PATENT DOCUMENTS

| | | | |
|---|---|---|---|
| 2002/0034486 A1* | 3/2002 | Midha | .................. A61K 8/0245 424/70.2 |
| 2008/0102051 A1 | 5/2008 | Huynh et al. | |
| 2009/0074697 A1 | 3/2009 | Huynh | |
| 2012/0093896 A1* | 4/2012 | Mongiat | .................. A61K 8/04 424/401 |

* cited by examiner

*Primary Examiner* — Robert A Wax
*Assistant Examiner* — Quanglong N Truong
(74) *Attorney, Agent, or Firm* — Polsinelli PC

(57) ABSTRACT

The present disclosure relates to leave-on hair styling compositions comprising: (a) one or more guar compounds: (b) one or more cellulose compounds; (c) one or more glycerol esters of fatty acids; and (d) water. The leave-on hair styling compositions do not require synthetic film-forming polymers nor do they require silicones. The leave-on hair styling compositions are particularly useful in methods for imparting durable styling or shaping benefits and/or frizz control to hair.

20 Claims, No Drawings

LEAVE-ON HAIR STYLING COMPOSITIONS AND METHODS OF USE

FIELD OF THE DISCLOSURE

The present disclosure relates to leave-on hair styling compositions for treating or styling hair. The leave-on hair styling compositions contain a combination of a guar compound, a cellulose compound, and a glycerol ester of fatty acids; and are useful in methods for imparting durable styling or shaping benefits, frizz control to hair, and general nourishing qualities to the hair.

BACKGROUND

Consumers desire new multi-functional hair products that can impart good styling benefits to hair, are durable and impart certain cosmetic characteristic to the hair. Such products should be pleasing to the senses, have innovative, interesting and/or pleasing textures, without loss in functional performance. Furthermore, many consumers prefer hair products that provide a light feel, are easy to apply, and add shine and luster to the hair.

Traditional hair products on the cosmetic market appear in various forms. They range anywhere from solutions, foams, gels, creams, waxes, mousses, sprays, serums, to aerosols and can impart a variety of levels of protection to the hair depending on the state of the hair and the components of the product. Generally, products that are designed to impart styling or shaping benefits to hair are in the form of hair styling or hair care/hair treatment products. Some of these products are often sticky or tacky upon application and once dry, may become stiff and/or "crunchy" (i.e. the film is hard and brittle resulting in a crunching feel or sound when the hair is touched), which is undesirable for many consumers.

Current products for imparting styling or shaping benefits to hair often include water soluble film-forming polymers. Depending on the chemical make-up of these polymers, they may be either soluble in water, or they may be water insoluble polymers which are made water soluble via various chemical modifications, such as neutralization. Solutions comprising these polymers tend to be viscous, i.e. as the concentration of the polymer increases, its viscosity builds up rapidly. Translated to styling applications, as the solvent evaporates, the polymer solution becomes thicker on the hair surface, resulting in a sticky or tacky film.

SUMMARY OF THE DISCLOSURE

The instant disclosure relates to leave-on hair styling compositions that are unique in their ability to impart a variety of desirable properties to hair. For example, the compositions provide a novel texture to the hair and maintain the shape of hair, achieve long-lasting frizz control, provide styling hold, and impart a pleasant shine and smoothness to hair without the use of synthetic film formers and/or silicones. Traditional hair styling products contain silicones, synthetic conditioning agents, and synthetic polymers in order to obtain a smooth look and feel. These synthetic materials however weigh down the hair, and cause the hair to feel dirty and greasy over time. Furthermore, because of the natural ingredients used in the compositions, upon application to the hair, the compositions have a clean, natural, and light-weight feel.

The leave-on hair styling compositions typically include: (a) one or more guar compounds; (b) one or more cellulose compounds; (c) one or more glycerol esters of fatty acids; and (d) water. In some cases, the leave-on hair styling composition may also include: (e) one or more fructan polysaccharides; (f) one or more monomeric polyols; and/or (g) one or more ester oils that are different than the one or more glycerol esters of fatty acids of (d).

Non-limiting examples of guar compounds include a guar gum, a cationic guar, hydroxypropyl guar, guar hydroxypropyl-trimethylammonium chloride, Hydroxypropyl guar hydroxypropyltrimethylammonium chloride, and mixtures thereof.

Non-limiting examples of cellulose compounds include a cellulose gum, methylcellulose, a hydroxypropyl cellulose, a hydroxypropyl methylcellulose, a hydroxyethyl cellulose, methylhydroxyethylcellulose, a hydroxyethyl carboxymethylcellulose, a carboxymethyl cellulose, a cationic cellulose, a sodium carboxymethyl cellulose, a microcrystalline cellulose, and mixtures thereof.

Non-limiting examples of glycerol esters of fatty acids include glyceryl monomyristate, glyceryl monopalmitate, glyceryl monostearate, glyceryl isostearate, glyceryl monooleate, glyceryl ester of mono(olive oil fatty acid), glyceryl dioleate, glyceryl distearate, trilaurin, triarachidin, tribehenin, tricaprin, tricaprylin, trierucin, triheptanoin, triheptylundecanoin, triisononanoin, triisopalmitin, triisostearin, trilinolein, trimyristin, trioctanoin, triolein, tripalmitin, tripalmitolein, triricinolein, tristearin, triundecanoin, and mixtures thereof.

Fructan polysaccharides include inulin polysaccharides and levan polysaccharides.

Non-limiting examples of monomeric polyols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, 1,6-hexanediol, 2-methyl-2,4-pentanediol, polyethylene glycol, 1,2,4-butanetriol, and 1,2,6-hexanetriol. Further, non-limiting examples of polyols comprising one or more aliphatic diols include 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and mixtures thereof.

Non-limiting examples of ester oils include ester oils selected from the group consisting of diisobutyl adipate, 2-hexyldecyl adipate, di-2-heptylundecyl adipate, monoisostearic acid N-alkyl glycol, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprate, triethyl citrate, 2-ethylhexyl succinate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, diisostearyl malate, dicaprylyl carbonate, and mixtures thereof.

Addition component may also optionally be included in the leave-on hair styling compositions, as set forth throughout the instant disclosure. Likewise, components may be excluded from the leave-on hair styling compositions. For instance, in some cases, the leave-on hair styling compositions are free or essentially free of synthetic film-forming polymers. In some cases, the leave-on hair styling compositions are free or essentially free of silicones.

Finally, leave-on hair styling compositions may be used in various methods for treating hair, for example, human hair, including human hair one an individual's head. For example, the compositions are useful for: (i) improving or retaining curl definition of hair; (ii) imparting humidity resistance to hair; (iii) reducing hair frizz; (iv) controlling hair volume; (v) styling hair; (vi) straightening hair; and (vi) improving the appearance of hair.

DETAILED DESCRIPTION OF THE DISCLOSURE

The leave-on hair styling compositions of the instant disclosure are useful for enhancing the appearance and feel of hair. The compositions include a unique combination of guar component(s), cellulose component(s), and glycerol esters of fatty acids. The synergy amongst these components results in compositions that provide desirable cosmetic properties to the hair, such as softening attributes, holding ability, and frizz control. The leave-on hair styling compositions typically include:

(a) one or more guar compounds;
(b) one or more cellulose compounds;
(c) one or more glycerol esters of fatty acids; and
(d) water.

Non-limiting examples of guar compounds include guar gum, a cationic guar, hydroxypropyl guar, guar hydroxypropyl-trimethylammonium chloride, Hydroxypropyl guar hydroxypropyltrimethylammonium chloride, and mixtures thereof. The total amount of the one or more guar components may vary, but is typically about 0.01 to about 20 wt. %, based on the total weight of the leave-on hair styling composition. In some cases, the total amount of the one or more guar components is about 0.01 to about 15 wt. %, about 0.01 to about 10 wt. %, about 0.01 to about 5 wt. %, about 0.1 to about 20 wt. %, about 0.1 to about 15 wt. %, about 0.1 to about 10 wt. %, about 0.1 to about 8 wt. %, about 0.1 to about 6 wt. %, or about 0.1 to about 5 wt. %, about 0.1 to about 5 wt. %, or about 0.1 to about 3 wt. %.

Non-limiting examples of cellulose compounds include those selected from the group consisting of a cellulose gum, methylcellulose, a hydroxypropyl cellulose, a hydroxypropyl methylcellulose, a hydroxyethyl cellulose, methylhydroxyethylcellulose, a hydroxyethyl carboxymethylcellulose, a carboxymethyl cellulose, a cationic cellulose, a sodium carboxymethyl cellulose, a microcrystalline cellulose, and mixtures thereof. In some cases, the leave-on hair styling compositions include at least cellulose gum. However, in some cases, the leave-on hair styling compositions include at least microcrystalline cellulose. In other cases, the leave-on hair styling compositions may include both cellulose gum and microcrystalline cellulose.

The total amount of the one or more cellulose components may vary, but is typically in an amount of about 0.1 to about 20 wt. %, based on the total weight of the leave-on hair styling composition. In some cases, the total amount of the one or more cellulose components is about 0.1 to about 15 wt. %, about 0.1 to about 10 wt. %, about 0.1 to about 8 wt. %, about 0.1 to about 6 wt. %, about 0.1 to about 5 wt. %, about 0.1 to about 4 wt. %, about 0.5 to about 20 wt. %, about 0.3 to about 15 wt. %, about 0.3 to about 10 wt. %, about 0.3 to about 8 wt. %, about 0.3 to about 6 wt. %, about 0.3 to about 5 wt. %, or about 0.3 to about 4 wt. %.

The ratio of the one or more guar components to the one or more cellulose components, in some cases, may be about 10:1 to about 1:10. The ratio of the one or more guar components to the one or more cellulose components may also about 5:1 to about 1:5, about 3:1 to about 1:3, or about 2:1 to about 1:2.

The leave-on hair styling compositions typically include one or more glycerol esters of fatty acids. Non-limiting examples of glycerol esters of fatty acids include those of the following formula:

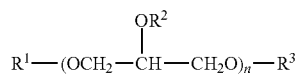

wherein n is 1, 2, or 3, and $R^1$, $R^2$ and $R^3$ each may independently be a $C_1$-$C_{40}$ fatty acid moiety or hydrogen, provided that at least one of $R^1$, $R^2$, and $R^3$ is a fatty acid moiety. More specific, non-limiting examples include glyceryl monomyristate, glyceryl monopalmitate, glyceryl monostearate, glyceryl isostearate, glyceryl monooleate, glyceryl ester of mono(olive oil fatty acid), glyceryl dioleate, glyceryl distearate, trilaurin, triarachidin, tribehenin, tricaprin, tricaprylin, trierucin, triheptanoin, triheptylundecanoin, triisononanoin, triisopalmitin, triisostearin, trilinolein, trimyristin, trioctanoin, triolein, tripalmitin, tripalmitolein, triricinolein, tristearin, triundecanoin, and mixtures thereof. In some instances, the leave-on hair styling compositions include one or more glycerol esters of fatty acids that are triglycerides, such as, for example, trilaurin, triarachidin, tribehenin, tricaprin, tricaprylin, trierucin, triheptanoin, triheptylundecanoin, triisononanoin, triisopalmitin, triisostearin, trilinolein, trimyristin, trioctanoin, triolein, tripalmitin, tripalmitolein, triricinolein, tristearin, triundecanoin, and mixtures thereof. In particular, at least tribehenin may be included in the leave-on hair styling compositions.

The total amount of the one or more polyglycerol esters of fatty acids may vary but is typically about 0.1 to about 20 wt. %, based on the total weight of the leave-on hair styling composition. In some cases, the total amount of the one or more polyglycerol esters of fatty acids is about 0.1 to about 15 wt. %, about 0.1 to about 10 wt. %, about 0.1 to about 8 wt. %, about 0.1 to about 6 wt. %, about 0.1 to about 5 wt. %, about 0.5 to about 20 wt. %, about 0.5 to about 15 wt. %, about 0.5 to about 10 wt. %, about 0.5 to about 8 wt. %, about 0.5 to about 6 wt. %, or about 0.5 to about 5 wt. %.

The leave-on hair styling compositions typically include water and therefore may be referred to as "aqueous compositions." The total amount of water can vary but is typically about 10 wt. % to about 95 wt. %, based on the total weight of the leave-on hair styling composition. The total amount of water may be about 20 wt. % to about 95 wt. %, about 30 wt. % to about 95 wt. %, about 40 wt. % to about 95 wt. %, about 50 to about 95 wt. %, about 60 to about 95 wt. %, about 70 wt. % to about 95 wt. %, about 80 wt. % to about 95 wt. %, or about 85 wt. % to about 92 wt. %.

Fructan polysaccharides (also referred to as just "fructan") are polymers of fructose molecules. Fructan polysaccharides include inulin polysaccharides (also referred to as just "inulin") and levan polysaccharide (also referred to as just "levan"). In some instances, the leave-on hair styling compositions include inulin polysaccharides; in some cases the leave-on hair styling compositions include levan polysaccharides; but in some cases the leave-on hair styling compositions may include both inulin and levan polysaccharides.

The total amount of the one or more fructan polysaccharides can vary, but is typically about 0.1 to about 40 wt. %, based on the total weight of the leave-on hair styling composition. The total amount of the one or more fructan polysaccharides may be about 0.1 to about 30 wt. %, about 0.1 to about 20 wt. %, about 0.1 to about 15 wt. %, about 0.1 to about 10 wt. %, about 0.1 to about 5 wt. %, about 1 to about 40 wt. %, about 1 to about 30 wt. %, about 1 to about 20 wt. %, about 1 to about 15 wt. %, about 1 to about 10 wt. %, or about 1 to about 5 wt. %.

In some cases, the leave-on hair styling compositions may include one or more monomeric polyols. Non-limiting examples of monomeric polyols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, 1,6-hexanediol, 2-methyl-2,4-pentanediol, polyethylene glycol, 1,2,4-butanetriol, and 1,2,6-hexanetriol. Further, non-limiting examples of monomeric polyols comprising one or more aliphatic diols include 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and mixtures thereof.

The total amount of the one or more polyols may vary, but typically is about 0.1 to about 50 wt. %, based on the total weight of the hair styling composition. The total amount of the one or more polyols may be about 0.1 to about 40 wt. %, about 0.1 to about 30 wt. %, about 0.1 to about 20 wt. %, about 0.1 to about 10 wt. %, about 0.1 to about 5 wt. %, about 0.5 to about 50 wt. %, about 0.5 to about 40 wt. %, about 0.5 to about 30 wt. %, about 0.5 to about 20 wt. %, about 0.5 to about 10 wt. %, or about 0.5 to about 5 wt. %

In some cases, the leave-on hair styling compositions can include one or more ester oils that are different than the one or more glycerol esters of fatty acids discussed above (as component (d)). In some cases, the one or more ester oils includes a monoester. Non-limiting examples of a monoester include those of the following formula:

$$R_5COOR_6 \quad (IV)$$

wherein $R_5$ represents a linear, branched, cyclic, saturated, unsaturated hydrocarbon-based group comprising from 4 to 40 carbon atoms, from 4 to 30 carbon atoms, or from 7 to 20 carbon atoms, a phenyl group, or a $R_5'$—O— group, wherein $R_5'$ represents a linear, branched, cyclic, saturated, unsaturated hydrocarbon-based chains comprising from 4 to 40 carbon atoms, from 4 to 30 carbon atoms, or from 7 to 20 carbon atoms, or a phenyl group; $R_6$ represents a linear, branched, cyclic, saturated, unsaturated hydrocarbon-based group comprising from 4 to 40 carbon atoms, from 4 to 30 carbon atoms, or from 7 to 20 carbon atoms, or phenyl group.

Non-limiting examples of ester oils that may be mentioned include isopropyl myristate, isopropyl palmitate, isononyl isononanoate, octyl isononanoate, tridecyl isononanoate, isopropyl myristate, triethyl hexanoin, diisostearyl maleate, glyceryl palmitate, glyceryl stearate, glyceryl diisostearate, glyceryl tri(caprylate/caprate), sorbitan isostearate, sorbitan stearate, sorbitan oleate, ethylhexyl stearate, decaprylyl carbonate, dodecyl benzoate, tetradecyl benzoate, hexadecyl benzoate, and mixtures thereof. Moreover, additional non-limiting examples of ester oils include diisobutyl adipate, 2-hexyldecyl adipate, di-2-heptylundecyl adipate, monoisostearic acid N-alkyl glycol, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprate, triethyl citrate, 2-ethylhexyl succinate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, diisostearyl malate, dicaprylyl carbonate, cetyl esters, and mixtures thereof.

Additional non-limiting examples of ester oils include diisobutyl adipate, 2-hexyldecyl adipate, di-2-heptylundecyl adipate, monoisostearic acid N-alkyl glycol, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprate, triethyl citrate, 2-ethylhexyl succinate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, diisostearyl malate, dicaprylyl carbonate, and mixtures thereof. In some cases, the leave-on hair styling compositions may include at least neopentyl glycol dicaprate, at least isopropyl myristate, at least dicaprylyl carbonate, or a combination of these ester oils (e.g., any two of the three components or all three components).

The total amount of the one or more ester oils may vary but is typically about 0.1 to about 50 wt. %, based on the total weight of the leave-on hair styling composition. In some cases, the total amount of the one or more ester oils is 0.1 to about 40 wt. %, about 0.1 to about 30 wt. %, about 0.1 to about 20 wt. %, about 0.1 to about 10 wt. %, about 0.1 to about 5 wt. %, about 0.5 to about 50 wt. %, about 0.5 to about 40 wt. %, about 0.5 to about 30 wt. %, about 0.5 to about 20 wt. %, about 0.5 to about 10 wt. %, about 0.5 to about 5 wt. %, about 1 to about 50 wt. %, about 1 to about 40 wt. %, about 1 to about 30 wt. %, about 1 to about 20 wt. %, about 1 to about 10 wt. %, or about 1 to about 5 wt. %.

The hair styling compositions of the instant disclosure are unique in that they do not require synthetic polymers such as synthetic film-forming polymers. In fact, the leave-on hair styling compositions do not necessarily require any synthetic ingredients. In some cases, synthetic film-forming polymer or synthetic polymer may be included but in other cases, they may be excluded. The term "synthetic polymer" (or "synthetic film-forming polymer") means a polymer, which is purely synthetic, or not of natural origin, especially those polymers, which are made by radical polymerization of ethylenically unsaturated monomers or by polycondensation. The term "natural polymer" means a polymer of natural origin, which includes those that have been subsequently chemically or physically modified (but retains at least 50% of its molecular structure from the original natural source). In particular, the term "natural original ingredient" refers to one of the following:

1. An ingredient which remains unchanged from its natural state; or

2. An ingredient which has undergone chemical or other processing which modifies it from its natural state but which retains at least 50% of its molecular structure from the original natural source.

In general, a naturally derived ingredient is processed to improve its stability, efficacy and/or safety for use in leave-on hair styling products. The degree of processing varies for each ingredient, but at the end only an ingredient that retains at least 50% of its molecular structure from the original natural source is considered natural origin. In some cases, the leave-on hair styling compositions of the instant disclosure are "natural leave-on hair styling compositions." A "natural leave-on hair styling composition" is a leave-on hair styling composition comprising only "natural original ingredients," as defined above.

Non-limiting examples of synthetic film-forming polymers (which in some cases may be excluded from the instant leave-on hair styling compositions) include non-ionic hair-fixing polymers (e.g., copolymerizates of vinyl pyrrolidone and vinyl acetate, terpolymers of vinyl pyrrolidone, vinyl acetate and vinyl propionate, polyacrylam ides, polyvinyl alcohols and polyethylene glycol/polypropylene glycol copolymers. Polyvinyl pyrrolidone, polyvinyl caprolactam and their copolymers with at least one further nonionic monomer, for example, polyvinylpyrrolidone/vinyl acetate copolymers) and anionic hair-fixing polymers such as synthetic homo- or copolymers with neutralizable monomer units containing acid groups, which are copolymerizable with comonomers, if necessary, which contain no acid groups. The acid groups may include —COOH, —SO$_3$H, —OSO$_3$H, —OPO$_2$H, —PO$_3$H$_2$. The acid groups can be unneutralized, or partially or completely neutralized.

Furthermore, the leave-in hair styling compositions do not require silicones (silicone and silicone containing materials). Non-limiting examples of silicones (which may optionally excluded from the instant leave-on hair styling compositions) include dimethicone, dimethiconol, amodimethicone, cyclomethicones, amino-modified silicones, and polyether-modified silicones In some instances, leave-on hair styling compositions of the instant disclosure include:
- (a) about 0.1 to about 10 wt. % of one or more guar compounds;
- (b) about 0.1 to about 10 wt. % of one or more cellulose compounds;
- (c) about 0.1 to about 20 wt. % of one or more glycerol esters of fatty acids;
- (d) water;
- (e) about 0.1 to about 20 wt. % of one or more fructan polysaccharides;
- (f) about 0.1 to about 10 wt. % one or more monomeric polyols; and
- (g) about 0.1 to about 20 wt. % one or more ester oils that are that are different that one or more glycerol esters of fatty acids (d).

In some cases, the one or more guar compounds is hydroxypropyl guar. Further, in some instances, the one or more cellulose compounds include microcrystalline cellulose, cellulose gum, or a mixture thereof.

In some cases, leave-on hair styling compositions of the instant disclosure include:
- (a) about 0.1 to about 5 wt. % one or more guar compounds;
- (b) about 0.1 to about 5 wt. % one or more cellulose compounds;
- (c) about 0.1 to about 20 wt. % of one or more glycerol esters of fatty acids;
- (d) water;
- (e) about 0.1 to about 5 wt. % of inulin;
- (f) about 0.1 to about 10 wt. % one or more monomeric polyols; and
- (g) about 0.1 to about 20 wt. % one or more ester oils that are that are different that one or more glycerol esters of fatty acids (d).

Again, in some cases, the one or more guar compounds is hydroxypropyl guar. Further, in some instances, the one or more cellulose compounds include microcrystalline cellulose, cellulose gum, or a mixture thereof.

In yet additional instances, the leave-on hair styling compositions of the instant disclosure include:
- (a) about 0.1 to about 5 wt. % of hydroxypropyl guar;
- (b) about 0.1 to about 5 wt. % of microcrystalline cellulose;
- (c) about 0.1 to about 20 wt. % of one or more glycerol esters of fatty acids;
- (d) water;
- (e) about 0.1 to about 5 wt. % of inulin;
- (f) about 0.1 to about 10 wt. % one or more monomeric polyols selected from the group consisting of glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, 1,6-hexanediol, 2-methyl-2,4-pentanediol, polyethylene glycol, 1,2,4-butanetriol, and 1,2,6-hexanetriol; and
- (g) about 0.1 to about 20 wt. % one or more ester oils that are that are different that one or more glycerol esters of fatty acids (d).

In some cases, the one or more polyols includes at least glycerin. Also, in some cases the one or more esters oils of (g) may be monoesters, for example, monoesters selected from the group consisting of isopropyl myristate, isopropyl palmitate, isononyl isononanoate, octyl isononanoate, tridecyl isononanoate, isopropyl myristate, triethyl hexanoin, diisostearyl maleate, glyceryl palmitate, glyceryl stearate, glyceryl diisostearate, glyceryl tri(caprylate/caprate), sorbitan isostearate, sorbitan stearate, sorbitan oleate, ethylhexyl stearate, decaprylyl carbonate, dodecyl benzoate, tetradecyl benzoate, hexadecyl benzoate, and mixtures thereof. Moreover, additional non-limiting examples of monoesters include diisobutyl adipate, 2-hexyldecyl adipate, di-2-heptylundecyl adipate, monoisostearic acid N-alkyl glycol, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprate, triethyl citrate, 2-ethylhexyl succinate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, diisostearyl malate, dicaprylyl carbonate, cetyl esters, and mixtures thereof.

The leave-on hair styling compositions described herein may be in any suitable physical form. Suitable forms include, but are not limited to low to moderate viscosity liquids, lotions, milks, mousses, sprays, gels, creams, pastes, clays, bars, conditioners, and the like. For instance, spray formulations may be dispensed from containers that include aerosol dispensers or pump spray dispensers. Such dispensers are known in the art and are commercially available from a variety of manufacturers. When the spray formulation is dispensed from a pressurized aerosol container, a propellant may be used to force the composition out of the container. Suitable propellants include, but are not limited to, a liquefiable gas or a halogenated propellant. Examples of suitable propellants include dimethyl ether and hydrocarbon propellants such as propane, n-butane, iso-butane, CFCs, and CFC-replacement propellants. The propellants may be used singly or admixed. Furthermore, the leave-on hair styling compositions may be in the form of an emulsion (e.g., water-in-oil or oil-in-water emulsion). In some cases, the leave-in hair styling composition is in the form of a paste, which may be a semi-solid product that can be applied throughout the hair using one's fingers.

As suggested by the term "leave-on hair styling compositions," these compositions are formulated so that they can remain on the hair for extended periods of time, i.e., the compositions are applied to the hair, for example, during styling of the hair and allowed to remain for one or more hours, or one or more days before being removed, for example, by washing. In other words, the leave-on hair styling compositions are applied to the hair and allowed to remain on the hair without immediate rinsing or removal. The leave-on hair styling compositions may be applied to the hair, for example, after shampooing, before or during the styling process. The hair may be wet, damp, or already dry when the hair styling composition is applied to the hair. In some cases, the leave-on hair styling composition may be applied to wet or damp hair after which the hair is blow dried and styled. In other cases, the hair may be previously dried and the leave-on hair styling composition is applied to dry hair, in order to treat, shape, or style the hair.

The leave-on hair styling compositions may be packaged in a variety of different containers, such as, for example, a ready-to-use container. Non-limiting examples of useful packaging include tubes, jars, caps, unit dose packages, and bottles, including squeezable tubes and bottles. The packaging may be configured so that it can be attached to a wall, such as a wall in a bathroom, including walls of a shower or tub. For example, the packaging can be a container that is configured to attach to a wall, such that when pressure is applied to the container, the composition contained therein is expelled from one or more openings in the bottom of the container.

The leave-on hair styling compositions may be used in various methods for treating hair, for example, human hair, including human hair one an individual's head. For example, the compositions are useful for: (i) improving or retaining curl definition of hair; (ii) imparting humidity resistance to hair; (iii) reducing hair frizz; (iv) controlling hair volume; (v) styling hair; (vi) straightening hair; and (vi) improving the appearance of hair; wherein the methods typically comprise applying a hair styling composition disclosed herein to the hair. These methods are particularly useful for naturally curly or frizzy hair. The hair styling compositions are useful in methods for imparting durable styling or shaping properties and/or frizz control to hair, the method comprising applying a hair styling composition to hair, including naturally curly or frizzy hair. The methods may include applying the leave-on hair styling composition to the hair, subsequently styling the hair while allowing the leave-on hair styling composition to remain on the hair, for example, for one or more hours, or one or more days before being removed by a subsequent washing. The leave-on hair styling composition may be applied to wet, damp, or already dry hair.

More exhaustive but non-limiting lists of components useful in the hair styling compositions disclosed herein are presented below.

Surfactants

Cationic Surfactants

The term "cationic surfactant" means a surfactant that is positively charged when it is contained in the composition according to the disclosure. This surfactant may bear one or more positive permanent charges or may contain one or more functions that are cationizable in the composition according to the disclosure.

Non-limiting examples of cationic surfactants include behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

Anionic Surfactants

The term "anionic surfactant" means a surfactant comprising, as ionic or ionizable groups, only anionic groups. These anionic groups are chosen preferably from the groups $CO_2H$, $CO_2^-$, $SO_3H$, $SO_3^-$, $OSO_3H$, $OSO_3^-$, $O_2PO_2H$, $O_2PO_2H$ and $O_2PO_2^{2-}$.

The anionic surfactant(s) that may be used may be alkyl sulfates, alkyl ether sulfates, alkylamido ether sulfates, alkylaryl polyether sulfates, monoglyceride sulfates, alkylsulfonates, alkylamide sulfonates, alkylarylsulfonates, alpha-olefin sulfonates, paraffin sulfonates, alkylsulfosuccinates, alkyl ether sulfosuccinates, alkylamide sulfosuccinates, alkyl sulfoacetates, acylsarcosinates, acylglutamates, alkylsulfosuccinamates, acylisethionates and N-acyltaurates, salts of alkyl monoesters and polyglycoside-polycarboxylic acids, acyllactylates, salts of D-galactoside uronic acids, salts of alkyl ether carboxylic acids, salts of alkyl aryl ether carboxylic acids, and salts of alkylamido ether carboxylic acids; or the non-salified forms of all of these compounds, the alkyl and acyl groups of all of these compounds containing from 6 to 24 carbon atoms and the aryl group denoting a phenyl group. Some of these compounds may be oxyethylenated and then preferably comprise from 1 to 50 ethylene oxide units.

The salts of $C_6$-$C_{24}$ alkyl monoesters of polyglycoside-polycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfo succinates.

When the anionic surfactant(s) are in salt form, they may be chosen especially from alkali metal salts such as the sodium or potassium salt and preferably the sodium salt, ammonium salts, amine salts and in particular amino alcohol salts, or alkaline-earth metal salts such as the magnesium salt.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts. Alkali metal or alkaline-earth metal salts and in particular the sodium or magnesium salts may be used.

Mention is also made of ($C_6$-$C_{24}$)alkyl sulfates, ($C_6$-$C_{24}$) alkyl ether sulfates, which are optionally ethoxylated, comprising from 2 to 50 ethylene oxide units, and mixtures thereof, in particular in the form of alkali metal salts or alkaline-earth metal salts, ammonium salts or amino alcohol salts. In some cases, the anionic surfactant(s) are chosen from ($C_{10}$-$C_{20}$)alkyl ether sulfates, and in particular sodium lauryl ether sulfate containing 2.2 mol of ethylene oxide.

Amphoteric Surfactants

Amphoteric surfactants useful in the cosmetic compositions disclosed herein may be chosen from betaines, sultaines, amphoacetates, amphoproprionates, and mixtures thereof. More typically, betaines and amphoproprionates are used, and most typically betaines. Betaines which can be used in the current compositions include those having the formulas below:

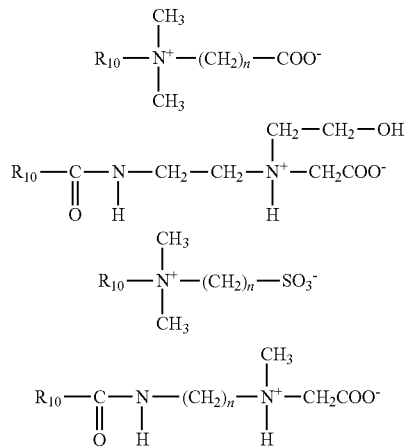

wherein $R^{10}$ is an alkyl group having 8-18 carbon atoms; and n is an integer from 1 to 3.

Particularly useful betaines include, for example, coco betaine, cocoamidopropyl betaine, lauryl betaine, laurylhydroxy sulfobetaine, lauryldimethyl betaine, cocoamidopropyl hydroxysultaine, behenyl betaine, capryl/capramidopropyl betaine, lauryl hydroxysultaine, stearyl betaine, and mixtures thereof. Typically, the at least one betaine compound is selected from the group consisting of coco betaine, cocoamidopropyl betaine, behenyl betaine, capryl/capramidopropyl betaine, lauryl betaine, and mixtures thereof, and more typically coco betaine.

Hydroxyl sultaines useful in the compositions of the invention include the following

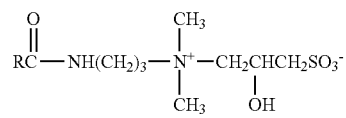

wherein

R is an alkyl group having 8-18 carbon atoms.

Useful alkylamphoacetates include those having the formula

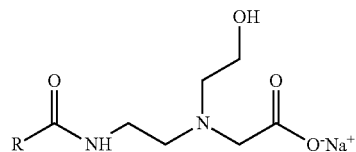

wherein

R is an alkyl group having 8-18 carbon atoms.

useful alkyl amphodiacetates include those having the formula

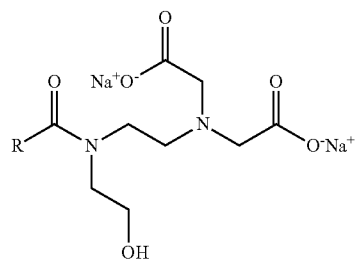

wherein

R is an alkyl group having 8-18 carbon atoms.

The amphoteric surfactants of the present disclosure may be optionally quaternized secondary or tertiary aliphatic amine derivatives, in which the aliphatic group is a linear or branched chain comprising from 8 to 22 carbon atoms, said amine derivatives containing at least one anionic group, for instance a carboxylate, sulfonate, sulfate, phosphate or phosphonate group.

Non-Ionic Surfactants

Nonionic surfactants are compounds well known in themselves (see, e.g., in this regard, "Handbook of Surfactants" by M. R. Porter, Blackie & Son publishers (Glasgow and London), 1991, pp. 116-178), which is incorporated herein by reference in its entirety.

The nonionic surfactant can be, for example, selected from alcohols, alpha-diols, alkylphenols and esters of fatty acids, these compounds being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4;

ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and mixtures thereof.

The nonionic surfactants may preferably be chosen from polyoxyalkylenated or polyglycerolated nonionic surfactants. The oxyalkylene units are more particularly oxyethylene or oxypropylene units, or a combination thereof, and are preferably oxyethylene units.

In some cases, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and mixtures thereof.

Examples of ethoxylated fatty esters that may be mentioned include the adducts of ethylene oxide with esters of lauric acid, palmitic acid, stearic acid or behenic acid, and mixtures thereof, especially those containing from 9 to 100 oxyethylene groups, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palm itostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof.

As glyceryl esters of fatty acids, glyceryl stearate (glyceryl mono-, di- and/or tristearate) (CTFA name: glyceryl stearate) or glyceryl ricinoleate and mixtures thereof can in particular be cited.

As glyceryl esters of $C_8$-$C_{24}$ alkoxylated fatty acids, polyethoxylated glyceryl stearate (glyceryl mono-, di- and/or tristearate) such as PEG-20 glyceryl stearate can for example be cited.

Mixtures of these surfactants, such as for example the product containing glyceryl stearate and PEG-100 stearate, marketed under the name ARLACEL 165 by Uniqema, and the product containing glyceryl stearate (glyceryl mono- and distearate) and potassium stearate marketed under the name TEG1N by Goldschmidt (CTFA name: glyceryl stearate SE), can also be used.

Cationic Conditioning Agents

The cationic conditioning agents that may be employed in the compositions of the present disclosure can be a monoalkyl quaternary amine, such as stearyltrimonium chloride, soyatrimonium chloride or coco-ethyldimonium ethosulfate. Other suitable cationic conditioning agents include, but are not limited to, behentrimonium chloride, dialkyl quaternary amines, such as dicetyldimonium chloride, dicocodimethyl ammonium chloride or distearyldimethyl ammonium chloride; and polyquaternium compounds, such as Polyquaternium-6, Polyquaternium-22 or Polyquaternium-5.

For example, cationic conditioning agents may be chosen from polyquaterium-10 (also called quaternized polyhydroxyethyl cellulose), cetrimonium chloride (also called cetyl trimethyl ammonium chloride, CTAC), behentrimonium chloride (also known as docosyl trimethyl ammonium chloride), behentrimonium methosulfate, steartrimonium chloride, stearalkonium chloride, dicetyldimonium chloride, hydroxypropyltrimonium chloride, cocotrimonium methosulfate, olealkonium chloride, steartrimonium chloride, babassuamidopropalkonium chloride, brassicamidopropyl dimethylamine, Quaternium-91, Salcare/PQ-37, Quaternium-22, Quaternium-87, Polyquaternium-4, Polyquaternium-6, Polyquaternium-11, Polyquaternium-44, Polyquaternium-67, amodimethicone, lauryl betaine, Polyacrylate-1 Crosspolymer, steardimonium hydroxypropyl hydrolyzed wheat protein, behenamidopropyl PG-dimonium chloride, lauryldimonium hydroxypropyl hydrolyzed soy protein, am inopropyl dimethicone, Quaterium-8, and dilinoleamidopropyl dimethylamine dimethicone PEG-7 phosphate.

In some instances, the cationic conditioning agents are cationic polymers. The term "cationic polymer" means any polymer comprising at least one cationic group and/or at least one group that may be ionized into a cationic group.

Particularly useful cationic polymers in the present invention include, but are not limited to, polyquaternium 4, polyquaternium 6, polyquaternium 7, polyquaternium 10, polyquaternium 11, polyquaternium 16, polyquaternium 22, polyquaternium 28, polyquaternium 32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, and guar hydroxypropyltrimonium chloride.

Particularly preferred cationic polymers of the present invention include POLYMER JR-125, POLYMER JR-400, Polymer JR-30M hydroxyethyl cellulosic polymers (polyquaternium 10) available from AMERCHOL; JAGUAR C® 13-S, guar hydroxypropyltrimonium chloride, available from Rhodia; and MERQUAT® 100 and 280, a dimethyl dialkyl ammonium chloride (polyquaternium 6) available from Nalco.

The cationic polymer is generally present in an amount of from greater than 0% to about 15%, preferably from about 0.5% to about 10% by weight, and more preferably from about 1% to about 5% by weight, based on the total weight of the composition.

Cationic polymers useful herein include polyquaternium 4, polyquaternium 6, polyquaternium 7, polyquaternium 10, polyquaternium 11, polyquaternium 16, polyquaternium 22, and polyquaternium 32. Cationic polymers useful in the present invention include, but are not limited to, polyquaternium 4, polyquaternium 6, polyquaternium 7, polyquaternium 10, polyquaternium 11, polyquaternium 16, polyquaternium 22, polyquaternium 28, polyquaternium 32, and guar hydroxypropyltrimonium chloride. Preferred cationic polymers include POLYMER JR-125, POLYMER JR-400, Polymer JR-30M hydroxyethyl cellulosic polymers (polyquaternium 10) available from AMERCHOL; JAGUAR C13-S, guar hydroxypropyltrimonium chloride, available from Rhodia; and MERQUAT 100 and 280, a dimethyl dialkyl ammonium chloride (polyquaternium 6) available from Nalco.

Oils

The hair styling composition may include one or more oils, for example, silicone oils, fluoro oils, hydrocarbon-based oils, etc. The term "oil" means any fatty substance which is in liquid form at room temperature (20-25° C.) and at atmospheric pressure (760 mmHg). Often, at least one of the oils in the cosmetic composition is part of an oily phase. An "oily phase" is a phase comprising at least one oil that may include additional liposoluble and lipophilic ingredients and the fatty substances. The oily phase can be combined with an aqueous phase in an emulsion. Oil that is suitable for use herein may be volatile or non-volatile. The term "volatile oil" relates to oil that is capable of evaporating on contact with the skin or a keratin fiber in less than one hour, at room temperature and atmospheric pressure. The volatile oil(s) are liquid at room temperature and have a non-zero vapor pressure, at room temperature and atmospheric pressure, ranging in particular from 0.13 Pa to 40 000 Pa ($10^{-3}$ to 300 mmHg). The term "non-volatile oil" relates to oil which remains on the skin or the keratin fiber, at room temperature and atmospheric pressure, for at least several hours and which in particular has a vapor pressure of less than $10^{-3}$ mmHg (0.13 Pa).

The term "silicone oil" relates to oil comprising at least one silicon atom, and especially at least one Si—O group. The term "fluoro oil" relates to oil comprising at least one fluorine atom. The term "hydrocarbon-based oil" relates to oil comprising mainly hydrogen and carbon atoms. Hydrocarbon-based oil may be animal hydrocarbon-based oil, plant hydrocarbon-based oil, mineral hydrocarbon-based oil or a synthetic hydrocarbon-based oil. Further, suitable oil may be a mineral hydrocarbon-based oil, a plant hydrocarbon-based oil, or a synthetic hydrocarbon-based oil.

Silicone Oils

The cosmetic compositions described herein may comprise one or more silicone oils. Non-limiting examples of silicone oils include dimethicone, cyclomethicone, polysilicone-11, phenyl trimethicone, trimethylsilylamodimethicone, and stearoxytrimethylsilane. In some cases, the cosmetic composition includes dimethicone, and optionally additional oils, including additional silicone oils. Typically, the one or more silicone oils is a non-volatile silicon oil. In some embodiments, the silicone oil is polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl) trimethylsiloxysilicates.

Other examples of silicone oils that may be mentioned include volatile linear or cyclic silicone oils, especially those with a viscosity 8 centistokes ($8 \times 10^6$ m$^2$/s) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Fluoro Oils

The cosmetic compositions described herein may comprise one or more fluoro oils. For example, the one or more fluoro oil may be selected from the group consisting of perfluoromethylcyclopentane, perfluoro-1,3-dimethylcyclohexane, dodecafluoropentane, tetradecafluorohexane, bromoperfluorooctyl, nonafluoromethoxybutane, nonafluoroethoxyisobutane and 4-trifluoromethylperfluoromorpholine. Volatile fluoro oils, such as nonafluoromethoxybutane, decafluoropentane, tetradecafluorohexane, dodecafluoropentane, may also be used.

Hydrocarbon-Based Oils

The cosmetic compositions described herein may comprise one or more hydrocarbon-based oils. For example, the hydrocarbon-based oil may be a saturated hydrocarbon, an unsaturated hydrocarbon, lipids, triglycerides, a natural oil, and/or a synthetic oil. In some embodiments, the compositions include a synthetic oil selected from the group consisting of hydrogenated polyisobutene and hydrogenated polydecene.

The hydrocarbon-based oil may be a non-volatile hydrocarbon-based, such as:

hydrocarbon-based oils of plant origin, such as glyceride triesters, which are generally triesters of fatty acids and of glycerol, the fatty acids of which can have varied chain lengths from $C_4$ to $C_{24}$, it being possible for these chains to be saturated or unsaturated and linear or branched; these oils are in particular wheat germ oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin seed oil, marrow oil, blackcurrant oil, evening primrose oil, millet oil, barley oil, quinoa oil, rye oil, safflower oil, candlenut oil, passionflower oil, and musk rose oil.

(ii) synthetic ethers containing from 10 to 40 carbon atoms;

(iii) linear or branched hydrocarbons of mineral or synthetic origin, such as petroleum jelly, polydecenes, hydrogenated polyisobutene such as Parleam, and 4 0 squalane;

(iv) synthetic esters, for instance oils of formula RCOOR' in which R represents a linear or branched fatty acid residue containing from 1 to 40 carbon atoms and R' represents a hydrocarbon-based chain that is especially branched, containing from 1 to 40 carbon atoms on condition that R+R' is 10, for instance Purcellin oil (cetearyl octanoate), isopropyl myristate, isopropyl palmitate, $C_{12}$-$C_{15}$ alkyl benzoate, such as the product sold under the trade name Finsolv TN® or Witconol TN® by Witco or Tegosoft TN® by Evonik Goldschmidt, 2-ethylphenyl benzoate, such as the commercial product sold under the name X-Tend 226 by ISP, isopropyl lanolate, hexyl laurate, diisopropyl adipate, isononyl isononanoate, oleyl erucate, 2-ethylhexyl palmitate, isostearyl isostearate, diisopropyl sebacate, such as the product sold under the name of "Dub Dis" by Stearinerie Dubois, octanoates, decanoates or ricinoleates of alcohols or polyalcohols, such as propylene glycol dioctanoate; hydroxylated esters, such as isostearyl lactate or diisostearyl malate; and pentaerythritol esters; citrates or tartrates, such as di(linear $C_{12}$-$C_{13}$ alkyl) tartrates, such as those sold under the name Cosmacol ETI® by Enichem Augusta Industriale, and also di(linear $C_{14}$-$C_{15}$ alkyl) tartrates, such as those sold under the name Cosmacol ETL® by the same company; or acetates;

(v) fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;

(vi) higher fatty acids, such as oleic acid, linoleic acid or linolenic acid;

(vii) carbonates, such as dicaprylyl carbonate, such as the product sold under the name Cetiol CC® by Cognis;

(viii) fatty amides, such as isopropyl N-lauroyl sarcosinate, such as the product sold under the trade name Eldew SL 205® from Ajinomoto; and (ix) essential oils selected from the group consisting of sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, and ylang ylang.

In certain instances, the non-volatile hydrocarbon-based oils are glyceride triesters and in particular to caprylic/capric acid triglycerides, synthetic esters and in particular isononyl isononanoate, oleyl erucate, $C_{12}$-$C_{15}$ alkyl benzoate, 2-ethylphenyl benzoate and fatty alcohols, such as octyldodecanol.

As volatile hydrocarbon-based oils, mention is made of hydrocarbon-based oils containing from 8 to 16 carbon atoms and in particular of branched $C_8$-$C_{16}$ alkanes, such as $C_8$-$C_{16}$ isoalkanes of petroleum origin (also known as isoparaffins), such as isododecane (also known as 2,2,4,4,6-pentamethylheptane), isodecane or isohexadecane, the oils sold under the Isopar or Permethyl trade names, branched C $C_8$-$C_{16}$ esters, and isohexyl neopentanoate.

Preservatives

One or more preservatives may be included in the compositions described herein for treating hair. Suitable preservatives include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), sodium benzoate, ethylenediamine-tetraacetic acid (EDTA), potassium sorbate, and/or grapefruit seed extract, or combinations thereof. More than one preservative may be included in the composition. Other preservatives are known in the cosmetics industries and include salicylic acid, DMDM Hydantoin, Formaldehyde, Chlorphenism, Triclosan, Imidazolidinyl Urea, Diazolidinyl Urea, Sorbic Acid, Methylisothiazolinone, Sodium Dehydroacetate, Dehydroacetic Acid, Quaternium-15, Stearalkonium Chloride, Zinc Pyrithione, Sodium Metabisulfite, 2-Bromo-2-Nitropropane, Chlorhexidine Digluconate, Polyaminopropyl biguanide, Benzalkonium Chloride, Sodium Sulfite, Sodium Salicylate, Citric Acid, Neem Oil, Essential Oils (various), Lactic Acid, and Vitamin E (tocopherol).

The total amount of the one or more preservatives, when present, may vary. In some cases, the total amount of the one or more preservatives is about 0.01 to about 5 wt. %, about 0.01 to about 4 wt. %, about 0.15 to about 1 wt. %, or about 1 to about 3 wt. %, based on the total weight of the composition.

Suitable components, such as those listed in the instant disclosure (including those listed above), may be included or excluded from the hair styling compositions depending on the specific combination of other components, the form of the compositions, and/or the use of the formulation (e.g., hair spray, cream, paste, conditioner, etc.).

Implementation of the present disclosure is provided by way of the following examples. The examples serve to illustrate the technology without being limiting in nature.

Example 1

| | (Hair Cream) | |
|---|---|---|
| | INCI US Name | 1<br>Wt. % |
| (a) | HYDROXYPROPYL GUAR | 0.5 |
| (b) | CELLULOSE GUM AND MICROCRYSTALLINE CELLULOSE | 0.6 |
| (c) | TRIBEHENIN | 1 |
| (d) | WATER | q.s. |
| (e) | INULIN | 1.9 |
| (f) | GLYCERIN | 2 |
| (g) | NEOPENTYL GLYCOL DICAPRATE, ISOPROPYL MYRISTATE, AND DICAPRYLYL CARBONATE | 2.5 |
| | CAPRYLYL GLYCOL | 0.5 |
| | SODIUM BENZOATE | 0.5 |
| | CETEARYL GLUCOSIDE | 0.2 |
| | CITRIC ACID | 0.1 |
| | CETEARYL ALCOHOL | 0.8 |
| | HONEY | 0.1 |
| | NATURAL EXTRACT | 0-1 |

Example 2

Contribution of Components

The individual influence of each of the main components of the hair cream of Example 1 was investigated. It was discovered that the combination of a guar compound and a cellulose compound provided a unique texture that could not be achieved using stand-alone thickeners. Furthermore, the combination of the guar compound and the cellulose compound provided appreciable slip and good feel to the hair.

It was found that hydroxypropyl guar used alone provided a slight gelling but did not afford an appropriate creamy texture. Also, xanthan gum used alone provided a slight gelling but did not provide an appropriate creamy texture. Microcrystalline cellulose (and) cellulose gum used alone did not provide sufficient thickness. Gellan gum used alone did not provide an appropriate rheology nor did it impart smoothing properties to the hair. Carrageenan used alone provided too much hold and stiffness.

Further testing was carried out to determine the influence of components useful for obtaining natural leave-on hair styling compositions. The results are presented in Table 1.

TABLE 1

Hair Styling Benefits

| Ingredient | Desired Texture | Desired Smoothness | Conditioning | Softness | Slip | Clean Feel | Shine |
|---|---|---|---|---|---|---|---|
| Microcrystalline Cellulose (and) Cellulose Gum | | | | | ✓ | ✓ | ✓ |
| Hydroxypropyl Guar | | | | | ✓ | ✓ | |
| Inulin | | ✓ | | ✓ | | ✓ | ✓ |
| Tribehenin | | | ✓ | ✓ | | ✓ | |
| Inulin + Tribehenin | | | ✓ | ✓ | | ✓ | |
| Microcrystalline Cellulose (and) Cellulose Gum + Hydroxypropyl Guar | ✓ | | | | ✓ | ✓ | ✓ |
| Microcrystalline Cellulose + Hydroxypropyl guar + inulin + tribehenin | ✓ | ✓ | ✓ | ✓ | ✓ | ✓ | ✓ |

"✓" indicates that the benefit reached an acceptable level.

A composition containing only hydroxypropyl guar provided slip, but did not thicken to an appropriate rheology. A composition containing only microcrystalline cellulose (and) cellulose gum provided slip, but did not thicken properly. A composition containing only inulin felt soft and gave some smoothing benefits, but did not have an appropriate degree of conditioning and slip. A composition containing only tribehenin provided softness and conditioning, but did not have an appropriate degree of smoothing benefit. A composition containing inulin and tribehenin provided softness, but did not provide an appropriate degree of slip and smoothing. A combination of a guar compound and a cellulose compound, however, provided significant smoothing and slip, but caused the hair to be more "straw" like and did not provide sufficient conditioning or natural feel. The synergy between the cellulose compound(s), the guar compound, inulin, and tribehenin provided a perfect balance between smoothing and conditioning while maintaining a clean feel.

Example 3

Cosmetic Attributes

The hair cream of Example 1 was evaluated by comparing its performance against a commercial benchmark product containing silicone and synthetic polymer. Ten volunteers participated. The volunteers' hair was shampooed. After shampooing, while the hair remained damp, the hair cream of Example 1 was applied to half of the head of each volunteer and the commercial benchmark product was applied to the other half of the head of each volunteer. After the hair was blown dry, experts evaluated the cosmetic attributes of the treated hair. The experts ranked a variety of attributes on a numerical scale, in most cases a scale of 1 to 5, where high numbers (e.g., 5) indicate better results. With respect to most attributes, the hair cream of Example 1 and the commercial benchmark product performed in parity (i.e., there was no statistical difference between the ranking for the various attributes). The statistically significant differences related to consistency, the degree of melting on hands, ease of distribution to hair tips, and wet hair combability. The hair cream of Example 1 melted noticeably more easily in the expert's hands, allowing the product to be easily applied from the hands to the hair. The commercial benchmark product, however, was rated as having noticeably better consistency. Also, the commercial benchmark product was rated as slightly better in terms of distribution to hair ends and wet combability. However, subsequent instrumental evaluations showed parity between the hair cream of Example 1 and the benchmark with respect to wet combability.

These findings with respect to the hair cream of Example 1 are significant because the hair cream of Example 1 does not contain silicone nor does it contain synthetic polymers, both of which are typically required to obtain satisfactory cosmetic attributes. Although the hair cream of Example 1 does not contain silicone or synthetic polymers, it performed largely on par with the commercial benchmark product. Furthermore, with respect to the few attributes for which the hair cream of Example 1 was deemed inferior to the commercial benchmark product, these attributes were nonetheless rated as better than average by the experts.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" are used in their open, non-limiting sense.

The terms "a," "an," and "the" are understood to encompass the plural as well as the singular.

The expression "one or more" means "at least one" and thus includes individual components as well as mixtures/combinations.

Other than in the operating examples, or where otherwise indicated, all numbers expressing quantities of ingredients and/or reaction conditions are to be understood as being modified in all instances by the term "about," meaning within +/−5% of the indicated number.

All percentages, parts and ratios herein are based upon the total weight of the compositions of the present disclosure, unless otherwise indicated.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

The term "substantially free" or "essentially free" as used herein means that there is less than about 2% by weight of a specific material added to a composition, based on the total weight of the compositions. The components described for optional inclusion in the compositions of the disclosure may be free of the component(s) or may be "substantially free" or "essentially free" of the component(s). Nonetheless, the compositions may include less than about 1 wt. %, less than about 0.5 wt. %, less than about 0.1 wt. %, or none of the specified material.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A leave-on hair styling composition comprising:
   (a) about 0.1 to about 10 wt. % of one or more guar compounds;
   (b) about 0.1 to about 10 wt. % of one or more cellulose compounds;
   (c) about 0.1 to about 20 wt. % of one or more glycerol esters of fatty acids;
   (d) water; and
   (e) about 0.1 to about 20 wt. % of one or more fructan polysaccharides.

2. The leave-on hair styling composition of claim 1, wherein the one or more guar compounds are selected from the group consisting of a guar gum, a cationic guar, hydroxypropyl guar, guar hydroxypropyl-trimethylammonium chloride, hydroxypropyl guar hydroxypropyltrimethylammonium chloride, and mixtures thereof.

3. The leave-on hair styling composition of claim 1, wherein the one or more cellulose compounds are selected from the group consisting of a cellulose gum, methylcellulose, a hydroxypropyl cellulose, a hydroxypropyl methylcellulose, a hydroxyethyl cellulose, methylhydroxyethylcellulose, a hydroxyethyl carboxymethylcellulose, a carboxymethyl cellulose, a cationic cellulose, a sodium carboxymethyl cellulose, a microcrystalline cellulose, and mixtures thereof.

4. The leave-on hair styling composition of claim 1 comprising one or more glycerol esters of fatty acids selected from the group consisting of glyceryl monomyristate, glyceryl monopalmitate, glyceryl monostearate, glyceryl isostearate, glyceryl monooleate, glyceryl ester of mono(olive oil fatty acid), glyceryl dioleate, glyceryl distearate, trilaurin, triarachidin, tribehenin, tricaprin, tricaprylin, trierucin, triheptanoin, triheptylundecanoin, triisononanoin, triisopalmitin, triisostearin, trilinolein, trimyristin, trioctanoin, triolein, tripalmitin, tripalmitolein, triricinolein, tristearin, triundecanoin, and mixtures thereof.

5. The leave-on hair styling composition of claim 1, wherein the one or more glycerol esters of fatty acids are triglycerides selected from the group consisting of trilaurin, triarachidin, tribehenin, tricaprin, tricaprylin, trierucin, triheptanoin, triheptylundecanoin, triisononanoin, triisopalmitin, triisostearin, trilinolein, trimyristin, trioctanoin, triolein, tripalmitin, tripalmitolein, triricinolein, tristearin, triundecanoin, and mixtures thereof.

6. The leave-on hair styling composition of claim 1 comprising about 20 to about 95 wt. % water.

7. The leave-on hair styling composition of claim 1, wherein the one or more fructan polysaccharides comprises inulin.

8. The leave-on hair styling composition of claim 1, further comprising:
   (f) one or more monomeric polyols.

9. The leave-on hair styling composition of claim 8, wherein the one or more monomeric polyols are selected from the group consisting of glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, 1,6-hexanediol, 2-methyl-2,4-pentanediol, polyethylene glycol, 1,2,4-butanetriol, and 1,2,6-hexanetriol.

10. The leave-on hair styling composition of claim 8 comprising about 0.1 to about 10 wt. % of the one or more monomeric polyols.

11. The leave-on hair styling composition of claim 1, further comprising:
    (g) one or more ester oils that are different than the one or more glycerol esters of fatty acids (d).

12. The leave-on hair styling composition of claim 11 comprising one or more ester oils selected from the group consisting of diisobutyl adipate, 2-hexyldecyl adipate, di-2-heptylundecyl adipate, monoisostearic acid N-alkyl glycol, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprate, triethyl citrate, 2-ethylhexyl succinate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, diisostearyl malate, dicaprylyl carbonate, and mixtures thereof.

13. The leave-on hair styling composition of claim 11 comprising about 0.1 to about 20 wt. % of the one or more ester oils.

14. A leave-on hair styling composition comprising:
    (a) about 0.1 to about 10 wt. % one or more guar compounds;
    (b) about 0.1 to about 10 wt. % one or more cellulose compounds;
    (c) about 0.1 to about 20 wt. % of one or more glycerol esters of fatty acids;
    (d) water;
    (e) about 0.1 to about 20 wt. % one or more fructan polysaccharides;
    (f) about 0.1 to about 10 wt. % one or more monomeric polyols; and
    (g) about 0.1 to about 20 wt. % one or more ester oils that are that are different than the one or more glycerol esters of fatty acids (d).

15. The leave-on hair styling composition of claim 1, wherein the composition is essentially free of synthetic film-forming polymers and essentially free of silicones.

16. The leave-on hair styling composition of claim 1 in the form of a spray, gel, foam, cream, emulsion, or paste.

17. The leave-on hair styling composition of claim 14 comprising:
    (a) about 0.1 to about 10 wt. % of hydroxypropyl guar;
    (b) about 0.1 to about 10 wt. % microcrystalline cellulose;
    (c) about 0.1 to about 20 wt. % tribehenin;
    (d) water;
    (e) about 0.1 to about 20 wt. % of inulin;
    (f) about 0.1 to about 10 wt. % of glycerin; and
    (g) about 0.1 to about 20 wt. % of neopentyl glycol dicaprate.

18. A method for shaping, imparting softness and/or smoothness, controlling fizz, improving shine, and enhancing discipline of hair comprising applying a leave-on hair styling composition of claim 1 to the hair.

19. A method for styling hair comprising applying a leave-on hair styling composition of claim 1 to the hair.

20. The leave-on hair styling composition of claim 14, wherein the one or more glycerol esters of fatty acids comprises one or more triglycerides.

* * * * *